(12) United States Patent
Vitali

(10) Patent No.: US 8,652,413 B2
(45) Date of Patent: Feb. 18, 2014

(54) MOBILE BODY DISINFECTION APPARATUS

(75) Inventor: Gastone Vitali, Civita Castellana (IT)

(73) Assignee: V.A.R.M. S.p.A., Civita Castellana (IT)

( * ) Notice: Subject to any disclaimer, the term of this patent is extended or adjusted under 35 U.S.C. 154(b) by 750 days.

(21) Appl. No.: 12/812,104

(22) PCT Filed: Dec. 30, 2008

(86) PCT No.: PCT/IB2008/003649
§ 371 (c)(1),
(2), (4) Date: Sep. 28, 2010

(87) PCT Pub. No.: WO2009/087466
PCT Pub. Date: Jul. 16, 2009

(65) Prior Publication Data
US 2011/0008221 A1 Jan. 13, 2011

(30) Foreign Application Priority Data
Jan. 10, 2008 (IT) .............................. BO2008A0014

(51) Int. Cl.
*A61L 2/18* (2006.01)
(52) U.S. Cl.
USPC ............................... 422/300; 422/292; 4/625
(58) Field of Classification Search
USPC ........................ 422/300, 292; 4/619, 625, 630
See application file for complete search history.

(56) References Cited

U.S. PATENT DOCUMENTS

| 4,130,123 A | 12/1978 | Wines et al. |
| 4,159,550 A | 7/1979 | Tobin |
| 5,702,115 A | 12/1997 | Pool |
| 6,173,458 B1 | 1/2001 | Maddux |

FOREIGN PATENT DOCUMENTS

| EP | 0529902 | 3/1993 |
| FR | 2790655 | 9/2000 |
| WO | WO 93/13276 | 7/1993 |
| WO | WO 00/53071 | * 9/2000 |
| WO | WO 2007/072422 | 6/2007 |

* cited by examiner

*Primary Examiner* — Sean E Conley
(74) *Attorney, Agent, or Firm* — Leason Ellis LLP

(57) ABSTRACT

A mobile body disinfection apparatus includes a carrying structure rendered mobile by means of a plurality of wheels attached thereto, a waste collection vessel, a liquid disinfectant dispensing element operated by a photoelectric cell and/or by a dispensing timer control, a filling tank, a supply line to carry the liquid disinfectant from the tank to the dispensing element, a waste tank connected to said washbasin, a drainage line and a central command and control unit suitable to manage at least the liquid disinfectant dispensing operations. The supply line comprises, in turn, at least one pump and one filter suitable to guarantee the elimination of infective elements that might be present in the water coming from the water distribution network and to guarantee a filtering of the liquid disinfectant that might have been contaminated even after filling the apparatus.

17 Claims, 10 Drawing Sheets

MOBILE BODY DISINFECTION APPARATUS

TECHNICAL FIELD

The present invention relates to a mobile body disinfection apparatus.

In particular the apparatus according to the present invention is an effective means for combating the transmission of infections via contact with contaminated hands in professional activities such as those of physicians, veterinary surgeons, etc.

BACKGROUND ART

The results of international studies have shown that each year the number of hospital infections transmitted via contact with contaminated hands is between 450,000 and 700,000, with an annual death rate of between 4,500 and 7,000. At least 30 percent of these could be prevented by correct and regular disinfection, which could reduce the number of deaths by about 2,000 each year. According to the above study the main cause of the majority of these infections is simply unclean hands. In many of the places where activities are performed, such as surgical dressing rooms and areas of transit in wards and corridors, there are no disinfection facilities that can easily be accessed by healthcare personnel, who should have convenient access to these and be able to disinfect themselves without any particular hindrance to their professional activities.

DISCLOSURE OF INVENTION

The purpose of the present invention is to produce a series of apparatus having technical characteristics such as to guarantee the disinfection of people in medical and healthcare environments regardless of the availability of access to the water and/or electricity distribution system.

The present invention relates to a mobile body disinfection apparatus as claimed in claim 1.

BRIEF DESCRIPTION OF THE DRAWINGS

In order to better understand the present invention, some non-limiting embodiments thereof will now be described by way of example with the help of the figures in the accompanying drawing, in which.

BEST MODE FOR CARRYING OUT THE INVENTION

Figure 1:
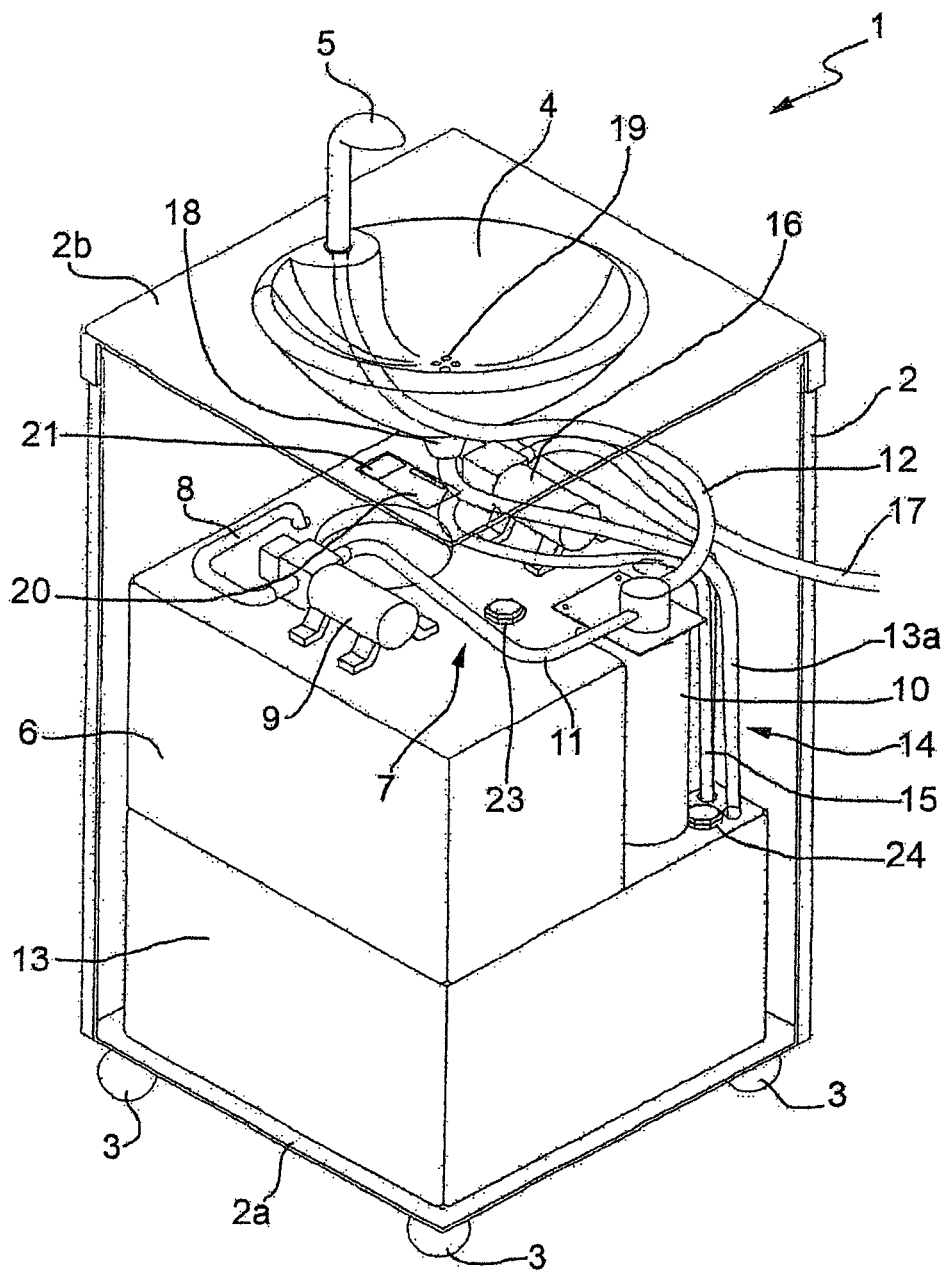
FIG. 1 is a perspective view with parts removed of a first embodiment of the mobile body disinfection apparatus according to the present invention.
Figure 2:
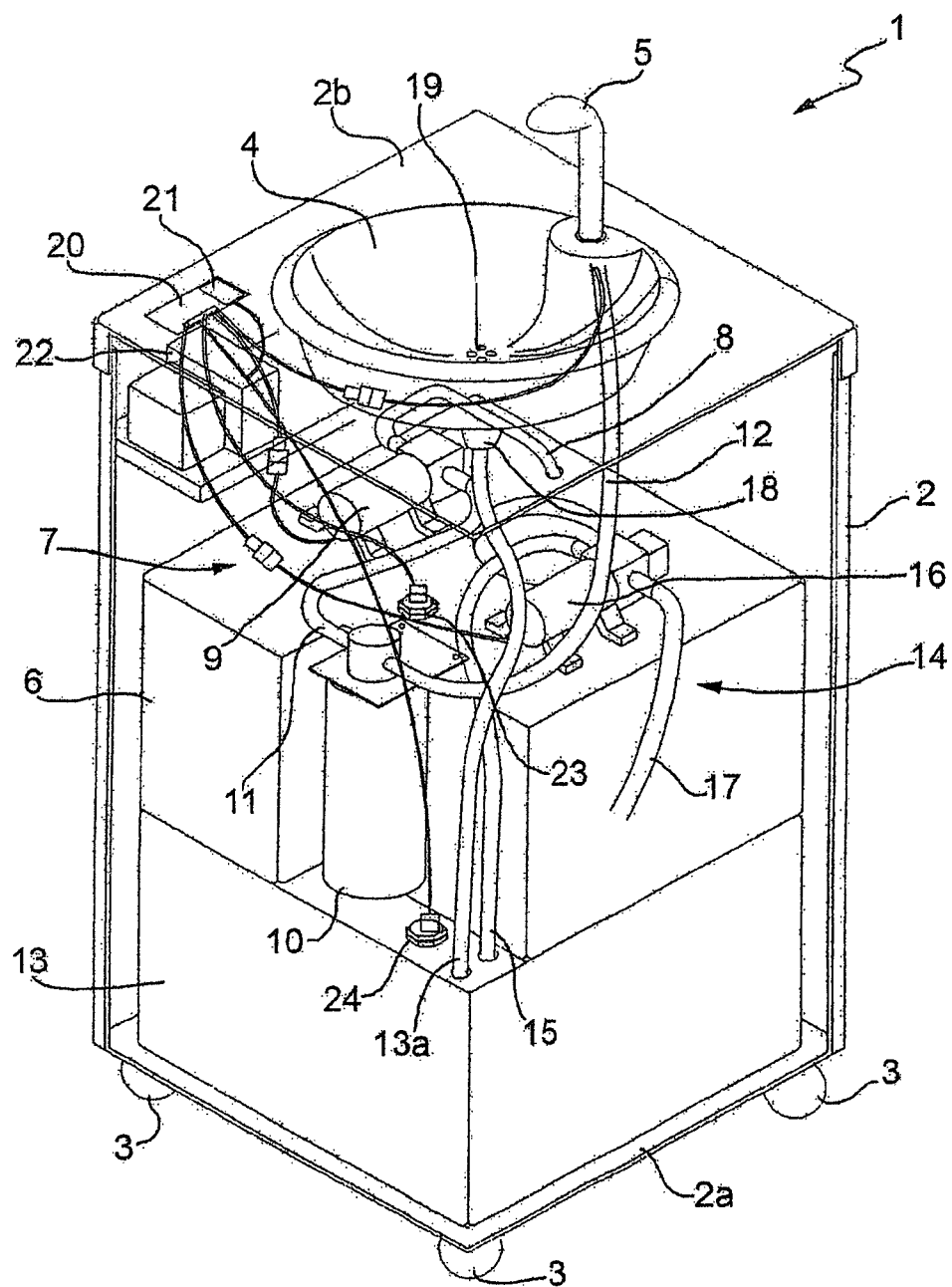
FIG. 2 is another perspective view with parts removed of the mobile apparatus of FIG. 1.

In FIGS. 1 and 2 designated as a whole by number 1 is the mobile body disinfection apparatus according to the present invention.

The mobile apparatus 1 comprises a carrying structure 2 that is parallelepiped in shape and provided with four wheels 3 attached to a base 2a thereof suitable to render it mobile. A ceramic washbasin 4 is set in an upper portion 2b of the carrying structure 2. An electronic tap 5 is mounted over said washbasin 4 and provided with a photoelectric cell which is not illustrated for the sake of simplicity.

Inside the carrying structure 2, the mobile apparatus 1 comprises a filling tank 6 and a supply line 7 to carry a liquid disinfectant from the tank 6 to the tap 5. Here and in the rest of this document, the term liquid disinfectant means either a mixture of water and a disinfectant product dissolved in the water or water that has been appropriately filtered as described below and which is used for disinfection.

The filling tank 6 may be insulated by means of suitable insulating material to enable the liquid disinfectant to be maintained at the right temperature for the entire working shift. A specific thermostat provides information on the temperature of the liquid.

The supply line 7 comprises an inlet pipe 8 that draws the liquid from the tank 6, a pump 9 connected to the inlet pipe 8 and suitable to guarantee the movement of the liquid disinfectant, a filter 10, a first connecting pipe 11 from the pump 9 to the filter 10 and a second connecting pipe 12 from the filter 10 to the tap 5. In particular, the filter 10 guarantees the elimination of bacteria, cysts, colloidal substances, legionella, etc., which may be present in the water coming from the water distribution network and at the same time guarantees the filtering of the liquid disinfectant that could have been contaminated even after filling the apparatus. The filter 10 used in the embodiment that is illustrated is marketed by EVERPURE S.A. under the name of MicroGuard™.

The inlet pipe 8 and the connecting pipes 11 and 12 are made of silicone to prevent the proliferation of bacteria.

Inside the carrying structure 2, the mobile apparatus 1 also comprises a waste tank 13 arranged beneath the filling tank 6, a pipe 13a connecting the waste tank 13 with the washbasin 4 and a drainage line 14. The drainage line 14 comprises an inlet pipe 15 that draws liquid from the tank 13, a pump 16 connected to the inlet pipe 15 and a drainage pipe 17.

The waste liquid is filtered through a specific filter 18 arranged on a drain 19 and, moreover, the waste tank can be specifically sanitized by means of processes capable of eliminating viruses and bacteria before being discharged into the sewerage system. Such treatment allows the waste water to be discharged into the sewerage system without bacteria, viruses, etc.

The mobile disinfection apparatus comprises an electric control unit 20, powered by a 12V battery or by a specific 12V power supply unit, which is used to control all the functions of the apparatus and includes luminous LEDs and information that is displayed on a screen 21 and any acoustic signals to interface with the user.

In particular, the control unit 20 is powered by means of a re-chargeable battery 22 and controls: the level of the liquids in the filling tank 6 and in the waste tank 13 by means of two respective level probes 23 and 24; the action of the two pumps 9 and 16, respectively to move the liquid disinfectant and the waste liquid; and the action of the electronic tap 5.

The control unit 20 also controls the charge level of the battery 21; it controls liquid filling by means of a pushbutton; and, optionally, it controls the timed dispensing of the liquid disinfectant through the tap 5, also by means of a pushbutton.

Another function of the control unit 20 is to guarantee safe operation and, thus, to interrupt dispensing when the filling tank 6 is empty, and when the waste tank 13 is full.

It will be clear from the above description that the body disinfection apparatus according to the present invention guarantees efficient disinfection thanks to the liquid disinfectant obtained by adding specific products to the water coming from the water distribution network, and to the thorough and effective filtering process by the filter 10 which thus prevents said water from constituting a potential source of infection.

Moreover, the apparatus is designed in such a way that the user does not come into contact with other sources of infection after the liquid disinfectant has been dispensed. The electronic tap 5 is provided with a photoelectric cell, via which an electric signal is sent to the pump 9, avoiding the need for the user to touch anything so that hand disinfection is performed simply and quickly. Alternatively, dispensing can be timed and controlled by means of a specific pushbutton. Dispensing timer control can be applied to a single tap or hand-held shower.

The use of the hand-held shower offers important advantages both in veterinary surgeries and for cleaning hospital patients who are unable to move. Moreover the liquid disinfectant flow can be adjusted to suit specific needs.

The mobile disinfection apparatus 1 comprises a filling pipe that is not illustrated, which connects the filling tank 6 to the water distribution network to supply water to said tank 6. This is done by pressing a filling button to open a filling valve of a type that is known and is not illustrated. The disinfectant products are introduced into the tank 6 before the water and dissolve in water to form the liquid disinfectant. It will be apparent that the disinfectant products must be chosen according to the specific use and type of activity to be performed.

Once the procedure to fill the tank 6 with water has been started, no other action is required. The control unit 20 controls the closing of the filling valve when the level probe 23 detects that the tank 6 is full.

The emptying procedure consists of placing the drainage pipe 17 in correspondence with a point of access to the sewerage system, such as a toilet or bidet, and sending a drain command via the control unit 20.

FIGS. 3-9 illustrate seven further embodiments of the mobile disinfection apparatus according to the present invention, which respond to specific needs depending on the level of mobility of the users, with no differences with respect to the description of the apparatus 1 as regards the characteristics for filling, dispensing and drainage.

Figure 3:
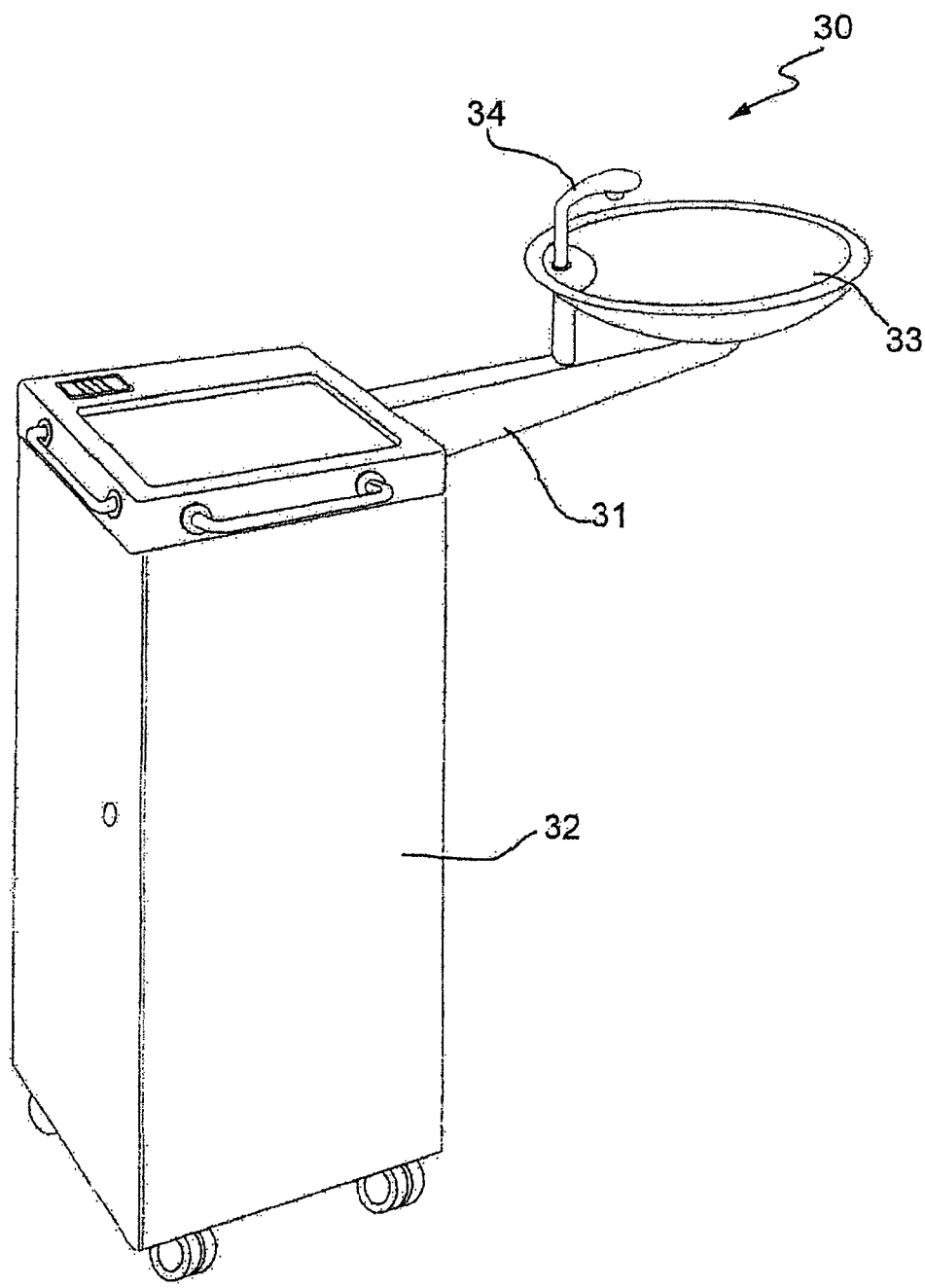
FIG. 3 is a perspective view of a second embodiment of the mobile apparatus according to the present invention.

In FIG. 3 designated as a whole with number 30 is a second embodiment of the mobile body disinfection apparatus according to the present invention. The apparatus 30 comprises a washbasin-holder arm 31 which extends from a carrying structure 32 and is suitable to support a washbasin 33 above which is mounted an electronic tap 34. The functional characteristics of the electronic tap 34 are the same as those described for the electronic tap 5 of the apparatus 1. The washbasin-holder arm 32 enables people who are unable to move to use the liquid disinfectant directly from the bed or chair.

Figure 4:
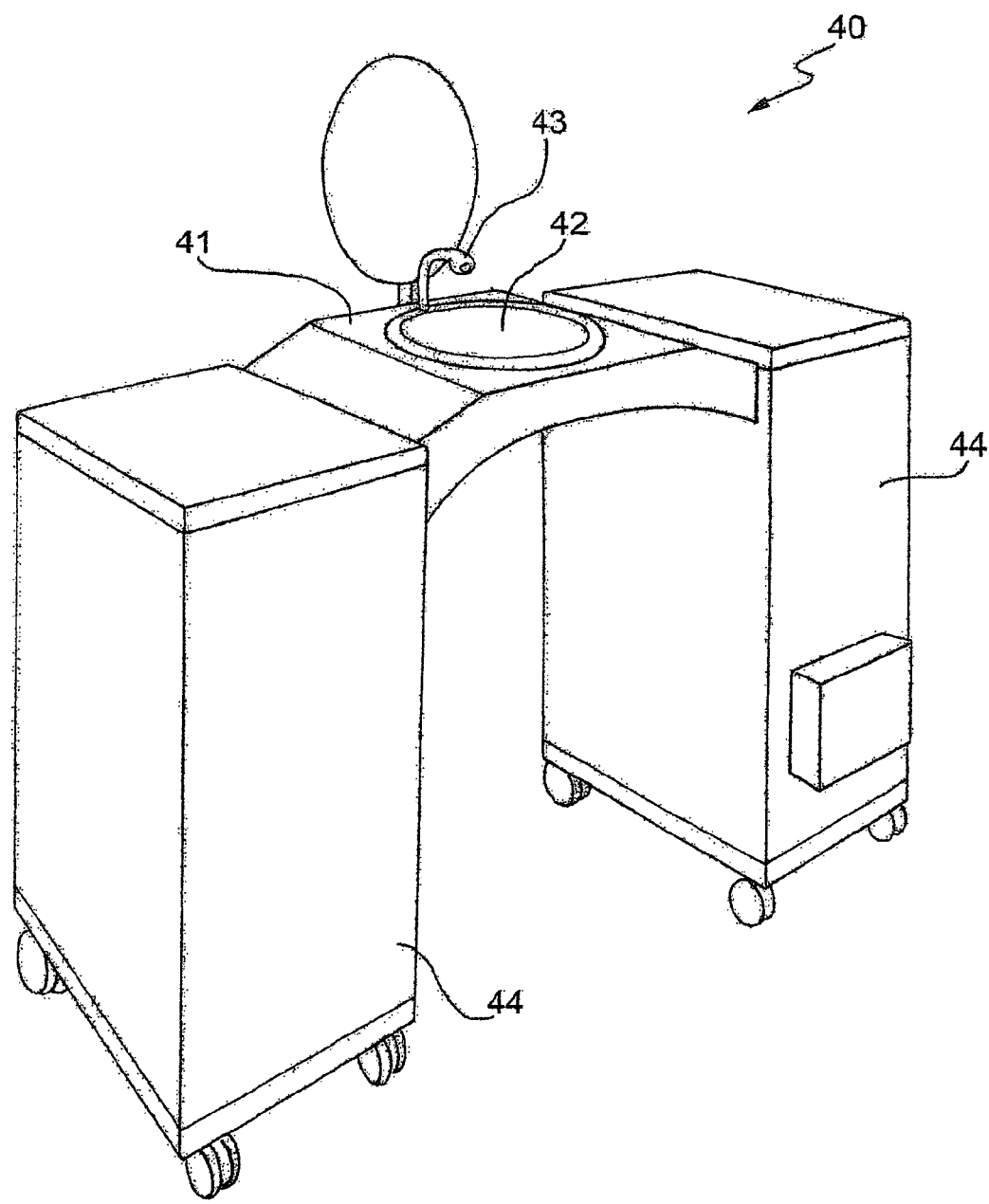
FIG. 4 is a perspective view of a third embodiment of the mobile apparatus according to the present invention.

In FIG. 4 designated as a whole with number 40 is a third embodiment of the mobile body disinfection apparatus according to the present invention. The apparatus 40 comprises a washbasin-holder bridge 41 suitable to support a washbasin 42 above which is mounted an electronic tap 43. The functional characteristics of the electronic tap 43 are the same as those described for the electronic tap 5 of the apparatus 1. The washbasin-holder bridge 41 rests on two column-type structures 44 at least one of which houses the filling, dispensing and drainage components housed inside the carrying structure 2 of the apparatus 1.

The apparatus 40 is particularly suitable for people confined to a wheelchair and can also be used outdoors, in places such as parks, gyms, swimming-pools, etc. with the possibility of fitting accessories such as a hairdryer, mirror, urine bottle.

Figure 5:
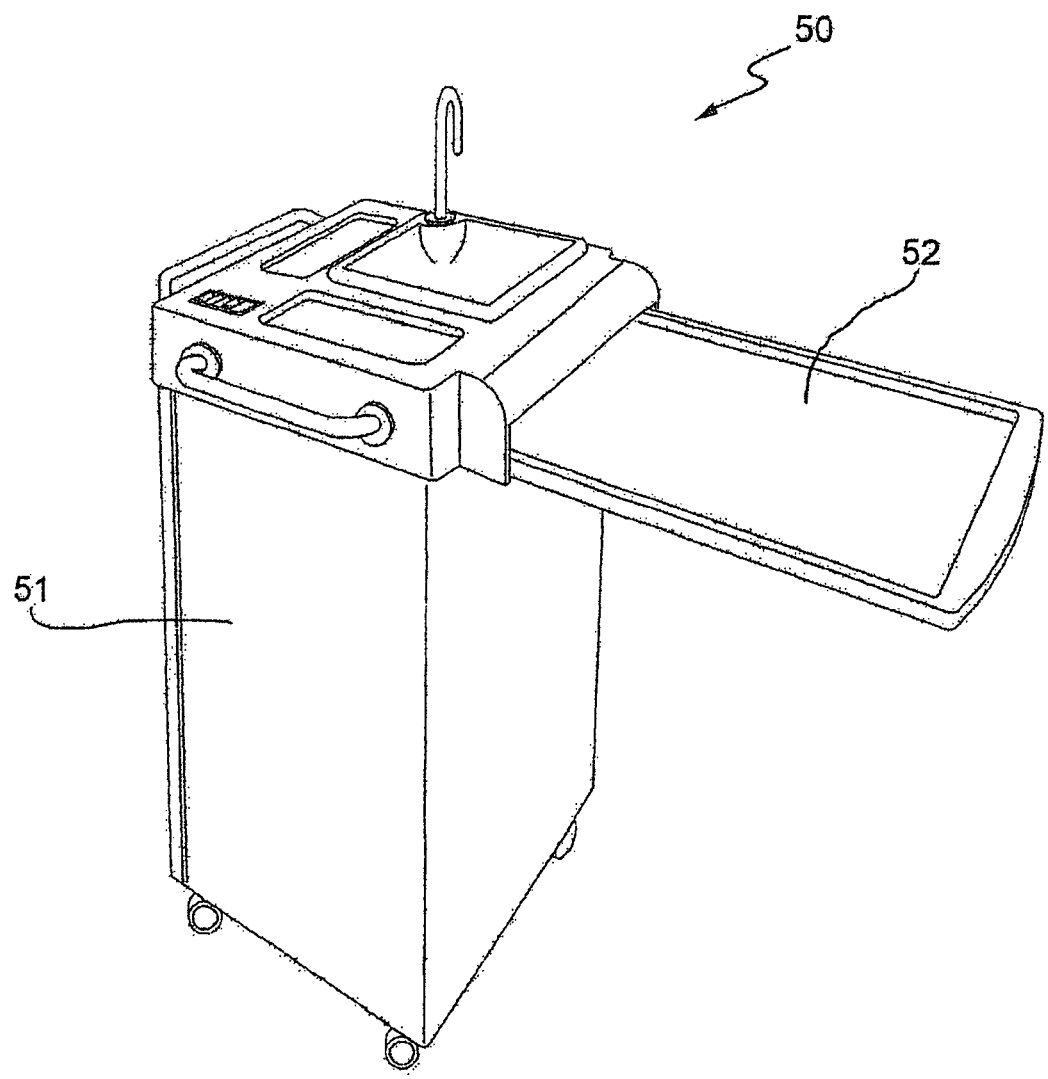
FIG. 5 is a perspective view of a fourth embodiment of the mobile apparatus according to the present invention.

In FIG. 5 designated as a whole with number 50 is a fourth embodiment of the mobile body disinfection apparatus according to the present invention. The apparatus 50 comprises a carrying structure 51 functionally the same as the carrying structure 2 of the apparatus 1, and a tray 52 suitable to assume a horizontal position or a vertical position resting against said carrying structure 51. In the horizontal position the tray 52 can be used as a table on which to serve meals to people who are bedridden or unable to move, making a source of liquid disinfectant available at the same time.

Figure 6:
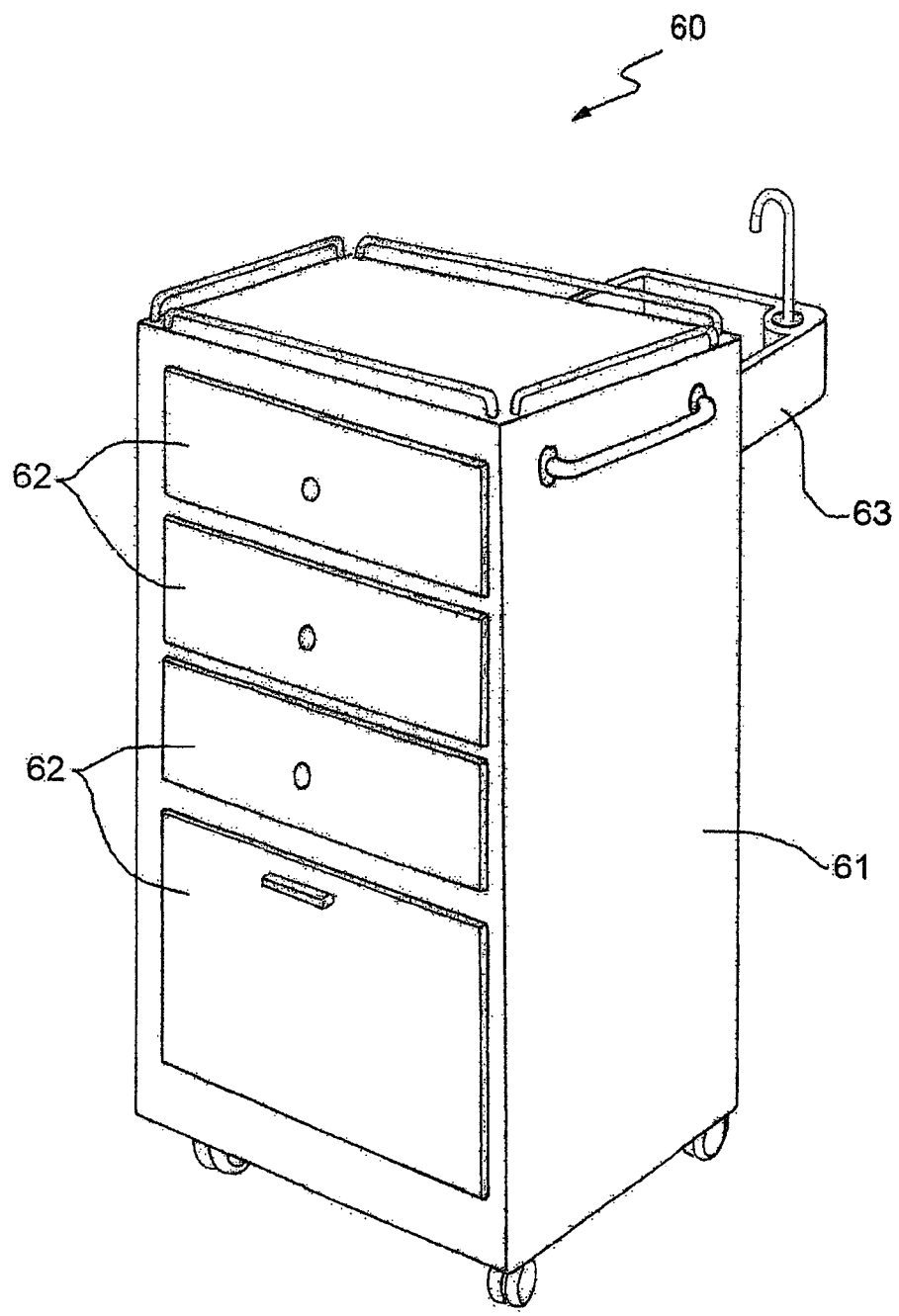
FIG. 6 is a perspective view of a fifth embodiment of the mobile apparatus according to the present invention.

In FIG. 6 designated as a whole with number 60 is a fifth embodiment of the mobile body disinfection apparatus according to the present invention. The apparatus 60 comprises a carrying structure 61 comprising, in turn, a plurality of drawers 62 which can be used to house medications and materials for disinfecting patients and healthcare workers such as for instance disinfectant gel, intravenous drips, blood bags, etc. The apparatus 60 comprises a washbasin 63 that can be pulled out from the carrying structure 61 like a drawer, so that it can be replaced inside the carrying structure 61 after use which is clearly advantageous in terms of convenience and mobility. The carrying structure 61 has the same functional characteristics as the carrying structure 2 of the apparatus 1.

Figure 7:
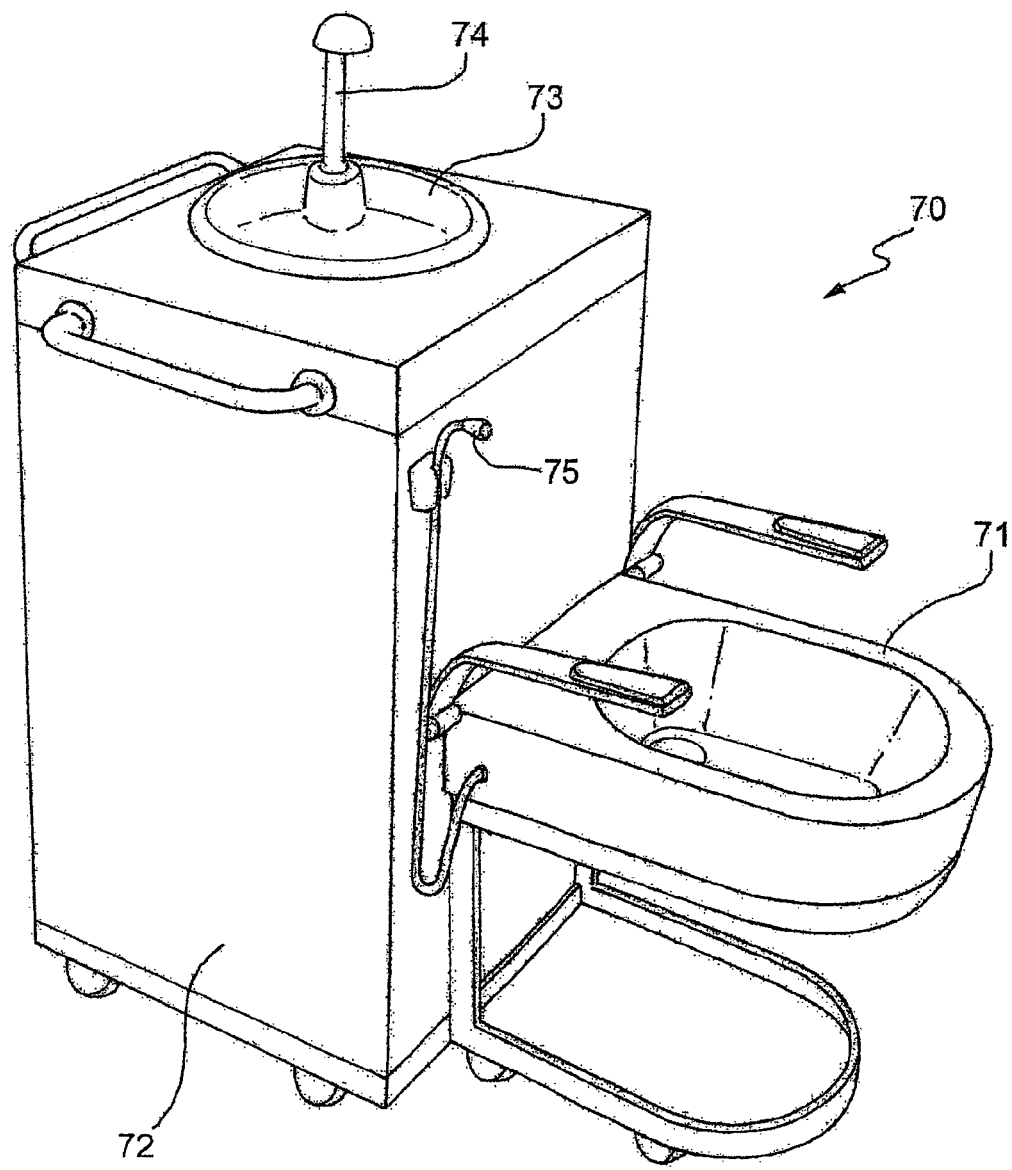
FIG. 7 is a perspective view of a sixth embodiment of the mobile apparatus according to the present invention.

In FIG. 7 designated as a whole with number 70 is a sixth embodiment of the mobile body disinfection apparatus according to the present invention. The apparatus 70 comprises a bidet 71 attached to a carrying structure 72 and connected to a waste tank inside the carrying structure and functionally the same as the waste tank 13 of the apparatus 1. The apparatus 70 is also provided with a washbasin 73 set in an upper part of the carrying structure 72. The apparatus 70 also comprises a tap 74 mounted above the washbasin 73 and a hand-held shower 75 for washing over the bidet 71. The tap 74 and the hand-held shower 75 have the same functional characteristics as the corresponding dispensing elements of the apparatus 1.

The apparatus 70 is particularly useful in gynaecology and urology departments, in particular for disinfecting patients before and/or after examinations or surgery.

It will be apparent that the apparatus 70 may also be provided without the washbasin 73 and is claimed as such.

Figure 8:
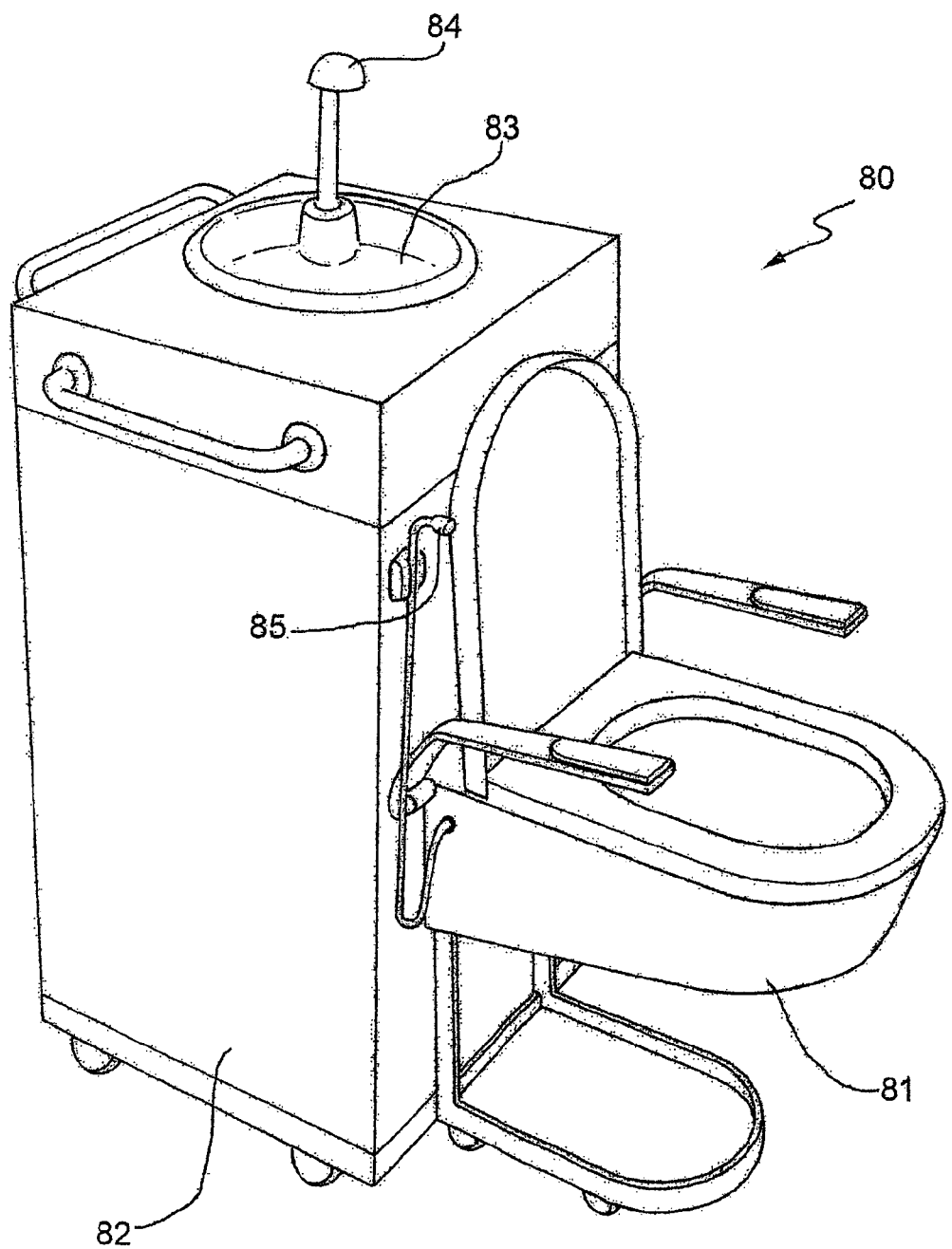
FIG. 8 is a perspective view of a seventh embodiment of the mobile apparatus according to the present invention.

In FIG. 8 designated as a whole with number 80 is a seventh embodiment of the mobile body disinfection apparatus according to the present invention. The apparatus 80 comprises a toilet 81 attached to a carrying structure 82 and connected to a waste tank inside the carrying structure 82 and functionally the same as the waste tank 13 of the apparatus 1. The apparatus 80 is also provided with a washbasin 83 set in an upper part of the carrying structure 82. The apparatus 80 also comprises a tap 84 mounted above the washbasin 83 and a hand-held shower 85 for washing over the toilet 81. The tap 84 and the hand-held shower 85 have the same functional characteristics as the corresponding dispensing elements of the apparatus 1.

Figure 8A:
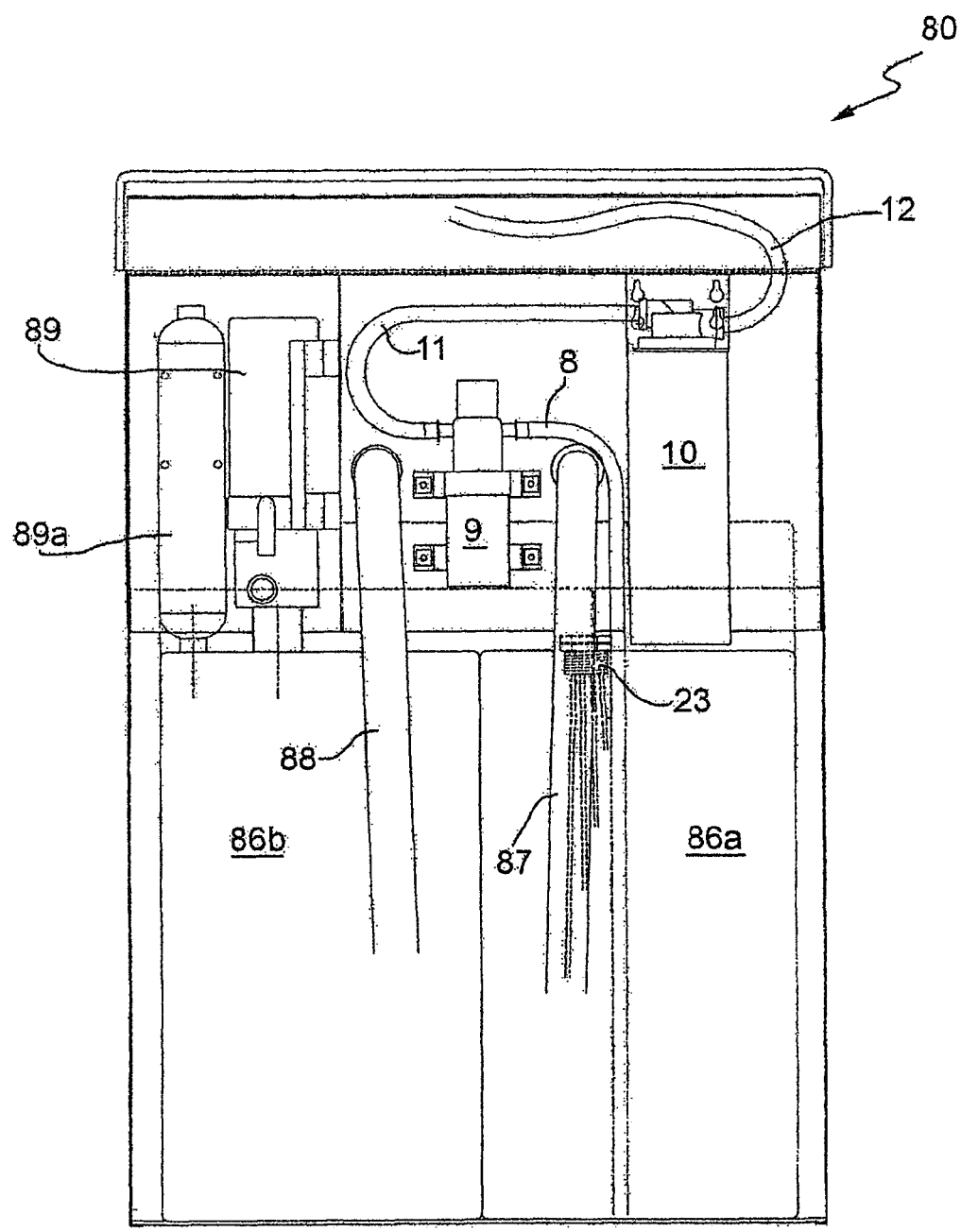
FIG. 8a is a rear view with parts removed of the embodiment of FIG. 8.

In FIG. 8a, the internal components of the apparatus 80 are partially illustrated. The components that are the same as those described in FIGS. 1 and 2 are designated with the same numbers and are not described again here.

The apparatus 80 comprises a filling tank 86a and a waste tank 86b arranged side by side. The apparatus 80 comprises a supply line 7 for carrying a liquid disinfectant from the tank 86a to the tap 84 and to the hand-held shower 85, a toilet flushing pipe 87 that draws in liquid from the tank 86a, a toilet drainage pipe 88 for draining the waste water from the toilet into the tank 86b, and a first grinder, of a type that is known and which is not described here, through which the waste water passes before entering the waste tank 86b. Lastly, the apparatus 80 comprises a second grinder 89, driven by a drainage pump that is not illustrated and is the same as the pump 16 of the apparatus 1 and through which the waste water passes when discharged from the waste tank 86b and an active carbon filter 89a connected to the waste tank 86b to eliminate foul odours.

The apparatus 80 is particularly useful in places where there are no toilet facilities or for people with reduced mobility.

Figure 9:
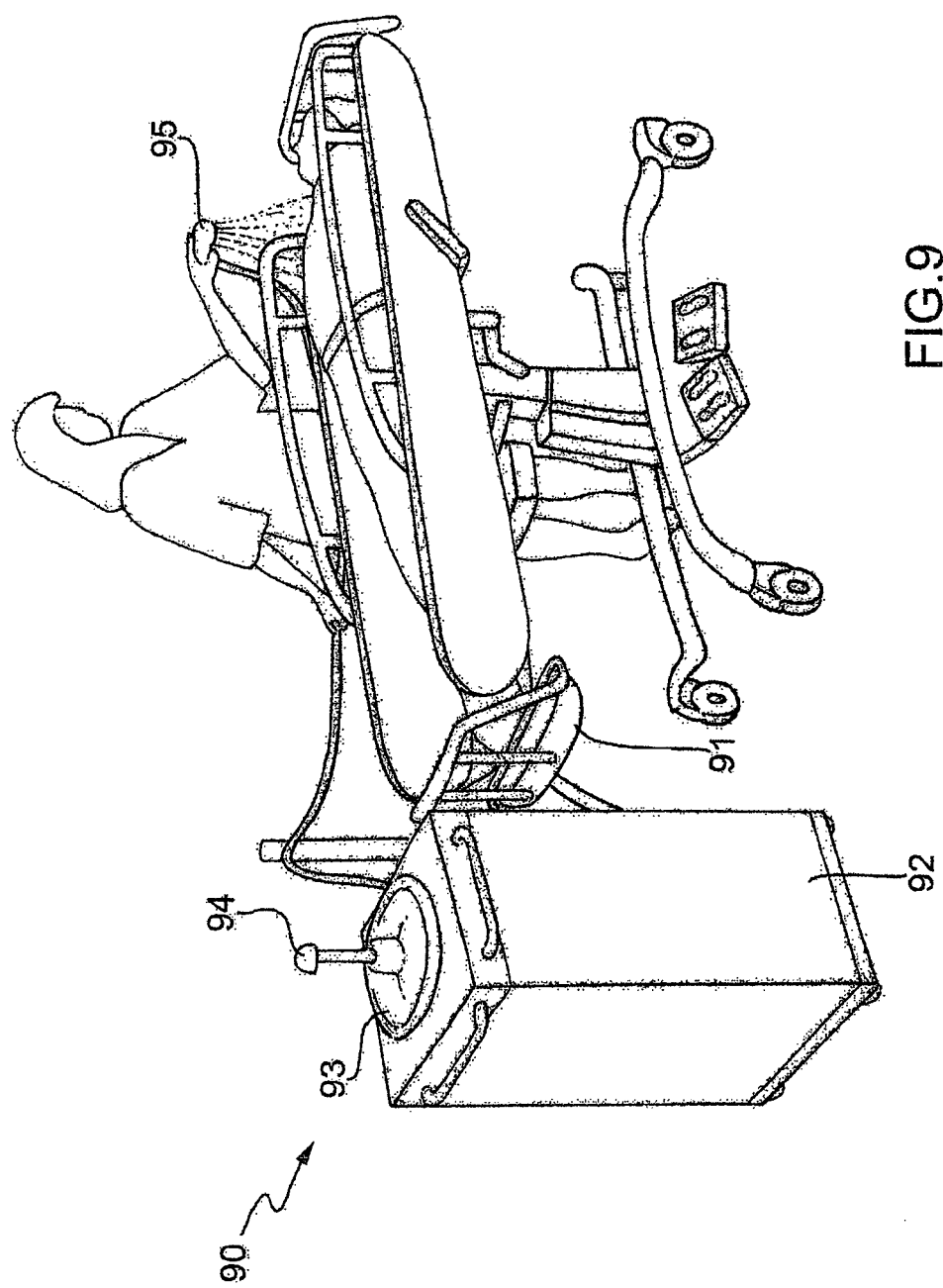
FIG. 9 is a perspective view of an eighth embodiment of the mobile apparatus according to the present invention.

In FIG. 9 designated as a whole with number 90 is an eighth embodiment of the mobile body disinfection apparatus according to the present invention. The apparatus 90 comprises a waste collection vessel 91 suitable to be arranged at one end of a stretcher trolley or bed and attached to a carrying structure 92. The waste collection vessel 91 is connected to a waste tank inside the carrying structure 92 and functionally the same as the waste tank 13 of the apparatus 1. The apparatus 90 is also provided with a washbasin 93 set in an upper part of the carrying structure 92. The apparatus 90 also comprises a tap 94 mounted above the washbasin 93 and a hand-held shower 95 for cleaning the patient, whether said patient is a person or animal, lying on the bed or on the stretcher trolley. The tap 94 and the hand-held shower 95 have the same functional characteristics as the corresponding dispensing elements of the apparatus 1.

The apparatus 90 is particularly suitable for washing and disinfecting people or animals that are unable to move and/or in accident and emergency units.

It will be apparent that the apparatus 90 may also be provided without the washbasin 93 and is claimed as such.

As described previously, the apparatus 30, 40, 50, 60, 70, 80 and 90 comprise dispensing, filling and drainage systems that are the same as those described and illustrated for the apparatus 1. More specifically, they comprise a filling tank, a waste tank, and a liquid disinfectant supply line, which is provided with a specific filter to eliminate bacteria, cysts, colloidal substances, legionella, etc. that might be present in the water coming from the water distribution network. Moreover, they include a filter for the waste water entering the waste tank and a central control and command unit for the overall operation and safety of the apparatus as described above for the apparatus 1.

The invention claimed is:

1. A mobile body disinfection apparatus comprising:
a carrying structure;
a waste collection vessel in the form of a toilet;
a liquid disinfectant dispensing element for dispensing a liquid disinfectant;
a filling tank for storing said liquid disinfectant;
a supply line to carry said liquid disinfectant from the filling tank to the dispensing element;
a waste tank connected to said waste collection vessel;
a drainage line;
at least one filter arranged on said supply line and suitable to guarantee the elimination of infective elements that might be present in the liquid disinfectant and a central control and command unit to manage at least the dispensing of said liquid disinfectant;
a first grinder through which waste liquid passes before entering the waste tank; and
a second grinder through which the waste liquid passes when discharged from the waste tank, wherein
said liquid disinfectant dispensing element is operated by at least one of photoelectric cell and a dispensing timer control,
the filling tank being insulated with insulating material to enable the liquid disinfectant to be maintained at the appropriate temperature for the entire working shift, and
said supply line comprising one or more pipes made of silicone to prevent the proliferation of bacteria.

2. The mobile body disinfection apparatus according to claim 1, characterized in that said drainage line comprises a filter suitable to sanitize the waste liquid before being discharged into the sewerage system.

3. The mobile body disinfection apparatus according to claim 1, further comprising two level probes respectively for said filling tank and said waste tank; said level probes being connected to said control unit.

4. The mobile body disinfection apparatus according to claim 1, characterized in that said dispensing element is one of a tap and a hand-held shower.

5. The mobile body disinfection apparatus according to claim 1, further comprising a washbasin-holder arm which extends from said carrying structure and is suitable to support a washbasin which comprises a second waste collection vessel.

6. The mobile body disinfection apparatus according to claim 1, further comprising a washbasin-holder bridge suitable to support a washbasin; said washbasin-holder bridge resting on two column-type structures at least one of which consists of said carrying structure.

7. The mobile body disinfection apparatus according to claim 1, further comprising a tray suitable to assume a horizontal position or a vertical position resting against said carrying structure.

8. The mobile body disinfection apparatus according to claim 1, further including a second waste collection vessel comprising a washbasin that can be pulled out from a carrying structure like a drawer.

9. The mobile body disinfection apparatus according to claim 1, further including a second waste collection vessel comprising one of a washbasin and a bidet.

10. The mobile body disinfection apparatus according to claim 1, further comprising:
a toilet flushing pipe that draws liquid from the filling tank; and
a toilet drainage pipe that discharges the waste liquid from the toilet into the waste tank.

11. The mobile body disinfection apparatus according to claim 1, further comprising a second waste collection vessel comprising one of a washbasin and vessel structure suitable to be arranged at one end of a stretcher trolley or bed.

12. The mobile body disinfection apparatus according to claim 1, wherein the central control and command unit controls the level of the liquid disinfectant in the filling tank and the waste tank.

13. The mobile body disinfection apparatus according to claim 1, further comprising a re-chargeable battery for powering the apparatus.

14. The mobile body disinfection apparatus according to claim 1, wherein the central control and command unit controls the charge level of the re-chargeable battery.

15. The mobile body disinfection apparatus according to claim 4, wherein the central control and command unit controls a timed dispensing of the liquid disinfectant through the dispensing element.

16. The mobile body disinfection apparatus according to claim 10, wherein an active carbon filter is connected to the waste tank to eliminate foul odors.

17. A mobile body disinfection apparatus comprising:

a carrying structure;

a first waste collection vessel in the form of a toilet that is connected to the carrying structure;

a second waste collection vessel in the form of a washbasin;

first and second liquid disinfectant dispensing elements;

a filling tank for storing liquid disinfectant;

supply lines to carry the liquid disinfectant from the filling tank to the first and second dispensing elements, wherein the first dispensing element comprises a controllable tap disposed above the wash basin and the second dispensing element comprises a hand-held shower that is located proximate the toilet for washing over the toilet, wherein the supply lines further include one supply line which delivers the liquid disinfectant from the filling tank into the toilet;

a waste tank connected to both the first and second waste collection vessels by means of respective conduits;

a drainage line for draining the waste tank;

at least one filter arranged on said supply line between the filling tank and the first dispensing element and configured to eliminate infective elements that might be present in the liquid disinfectant and a central control and command unit to manage at least the dispensing of said liquid disinfectant;

a first grinder located within a toilet drainage conduit between the toilet and the waste tank through which liquid waste passes before entering the waste tank; and a second grinder located within a conduit through which the liquid waste passes when discharged from the waste tank;

wherein the first disinfectant dispensing element is operated by at least one of a photoelectric cell and a dispensing timer control for controlled release of liquid disinfectant under predetermined conditions;

wherein the filling tank is insulated with insulating material to enable the liquid disinfectant to be maintained at the appropriate temperature for the entire working shift; and wherein the supply line comprises one or more pipes made of silicone to prevent the proliferation of bacteria.

* * * * *